United States Patent [19]
Tanimoto et al.

[11] Patent Number: 5,087,369
[45] Date of Patent: Feb. 11, 1992

[54] FLUIDIZED BED SEPARATION AND RECOVERY OF PROTEINS FROM FLUIDS IN A ROTARY COLUMN

[75] Inventors: Morimasa Tanimoto, Sayama; Kaoru Sato, Kawagoe; Shinichi Dosako, Urawa; Yoshihiko Honda, Sapporo, all of Japan

[73] Assignee: Snow Brand Milk Products Co., Ltd., Sapporo, Japan

[21] Appl. No.: 643,988

[22] Filed: Jan. 22, 1991

Related U.S. Application Data

[63] Continuation-in-part of Ser. No. 385,513, Jul. 27, 1989, abandoned.

[30] Foreign Application Priority Data

Jul. 27, 1988 [JP] Japan .................. 63-187400

[51] Int. Cl.⁵ .................................. B01D 15/08
[52] U.S. Cl. .................... 210/635; 210/657; 210/198.2; 426/491; 530/395; 530/413; 530/417
[58] Field of Search .............. 426/491; 530/395, 413, 530/417; 210/635, 656, 657, 198.2, 267, 502.1, 772, 784

[56] References Cited

U.S. PATENT DOCUMENTS

| | | | |
|---|---|---|---|
| 4,072,667 | 2/1978 | Ishida | 530/416 |
| 4,111,660 | 9/1978 | Kabasawa | 422/258 |
| 4,116,948 | 9/1978 | Mittenzwei | 210/657 |
| 4,156,681 | 5/1979 | Schneider | 530/830 |
| 4,190,530 | 2/1980 | Forsythe | 210/267 |
| 4,242,450 | 12/1980 | Honda | 435/69 |
| 4,422,941 | 12/1983 | Vaughan | 210/657 |
| 4,663,163 | 5/1987 | Hou | 210/635 |
| 4,667,018 | 5/1987 | Prieels | 530/417 |
| 4,668,771 | 5/1987 | Kawakami | 530/413 |
| 4,675,113 | 6/1987 | Graves | 210/635 |
| 4,741,998 | 5/1988 | Herr | 530/387 |
| 4,791,193 | 12/1988 | Oko . | |

FOREIGN PATENT DOCUMENTS

56-43228 10/1981 Japan .................. 210/198.2

Primary Examiner—Ernest G. Therkorn
Attorney, Agent, or Firm—Millen, White & Zelano

[57] ABSTRACT

Disclosed is a method for separating and recovering very small amounts of biologically active proteins (such as enzymes, antigens and antibodies) present in a various fluids, with a high recovery and on a large scale, in which a fluid containing a desired protein is introduced into a rotary column through orifices therein and brought into contact with a gel carrier capable of selectively adsorbing the desired protein, while the carrier is being gentle fluidized in a liquid by the rotary motion successively by wash water and eluting fluid, so that the column, after which the fluid is displaced, the carrier having the desired protein adsorbed thereon is washed and the desired protein is recovered therefrom by elution while the carrier fluidized.

10 Claims, 1 Drawing Sheet

⇐ FLOW

FLUIDIZED BED SEPARATION AND RECOVERY OF PROTEINS FROM FLUIDS IN A ROTARY COLUMN

FLUIDIZED BED SEPARATION AND RECOVERY OF PROTEINS FROM FLUIDS IN A ROTARY COLUMN

This is a continuation-in-part of application Ser. No. 07/385,513, filed July 27, 1989, now abandoned.

BACKGROUND OF THE INVENTION

1. Field of the Invention

This invention relates to a method for efficiently separating and recovering useful proteins present in various fluids, and in particular, useful proteins present in very small amounts.

2. Description of the Prior Art

Conventionally, in order to separate and purify proteins by means of a so-called affinity gel carrier, the use of a packed-bed column has been common in laboratory practice and in small-scale industrial production.

However, packed-bed columns have the disadvantage that, when a large volume of fluid is passed through a packed-bed column, as in cases where it is desired to separate and purify very small amounts of physiologically active proteins present in milk, the adsorption efficiency is rapidly reduced owing, for example, to densification of the carrier. In order to keep the adsorption efficiency satisfactorily high, it is necessary to decrease the volume of fluid passed through the column. However, this is disadvantageous from a practical point of view in that the passage time becomes too long to be suitable for the treatment of large volumes of fluid.

There has also been proposed a method for effecting the adsorption by passing a fluid through a fluidized-bed column in a so-called batchwise operation. However, this method involves long-term mechanical agitation and the carrier is very susceptible to damage.

In order to prevent the carrier from being damaged, an attempt has been made to fluidize the carrier by the action of an upflow. However, since this requires a high carrier sedimentation rate, it becomes necessary to enlarge the particle diameter of the carrier or enhance the density of the carrier. Thus, this method had the disadvantage that the type of carrier usable therein is limited.

Meanwhile, a rotary column reactor for activating an immobilized enzyme efficiently has recently been developed (Japanese Patent Publication No. 43228/'81). This reactor consists of a rotary column having an immobilized enzyme placed therein and a housing for enclosing the rotary column, and is intended to achieve efficiently the purpose of activating the immobilized enzyme placed therein and washing it after its use. It is not known whether this reactor can serve to recover very small amounts of useful proteins present in various fluids.

SUMMARY OF THE INVENTION

The present inventors have made an intensive study of the method of efficiently separating and recovering very small amounts of useful proteins present in various fluids, and have found that the desired protein can be effectively adsorbed, washed and eluted by using an affinity gel carrier, by fluidizing the carrier and bring the fluid containing the protein and the wash and eluting liquids successively into contact with the carrier while the carrier is in a state of turbulent flow. The present invention has been completed on the basis of this finding.

According to the present invention, there is provided a method for separating and recovering a specific protein (or proteins) from a protein-containing fluid by means of an affinity gel carrier, which comprises the steps of charging the affinity gel carrier into a rotary column; passing the protein-containing fluid through the column by way of orifices while rotating the column to fluidize the carrier, whereby the fluid comes into contact with the carrier in a state of turbulent flow and the protein contained therein becomes adsorbed on the carrier; washing the column by passing a washing liquid through the column being rotated; and eluting the desired protein from the washed column by passing an eluent through the column being rotated.

According to the method of the present invention, the efficiency of contact between an affinity gel carrier and a protein-containing fluid can be greatly enhanced under mild conditions. Thus, even when the content of a useful protein in the fluid is very low, the protein can be effectively recovered by treating the fluid on a large scale. Moreover, the protein present in the fluid can be advantageously recovered without causing any significant damage to the carrier used to adsorb the protein thereon.

DETAILED DESCRIPTION AND THE PREFERRED EMBODIMENTS

Figure 1A:
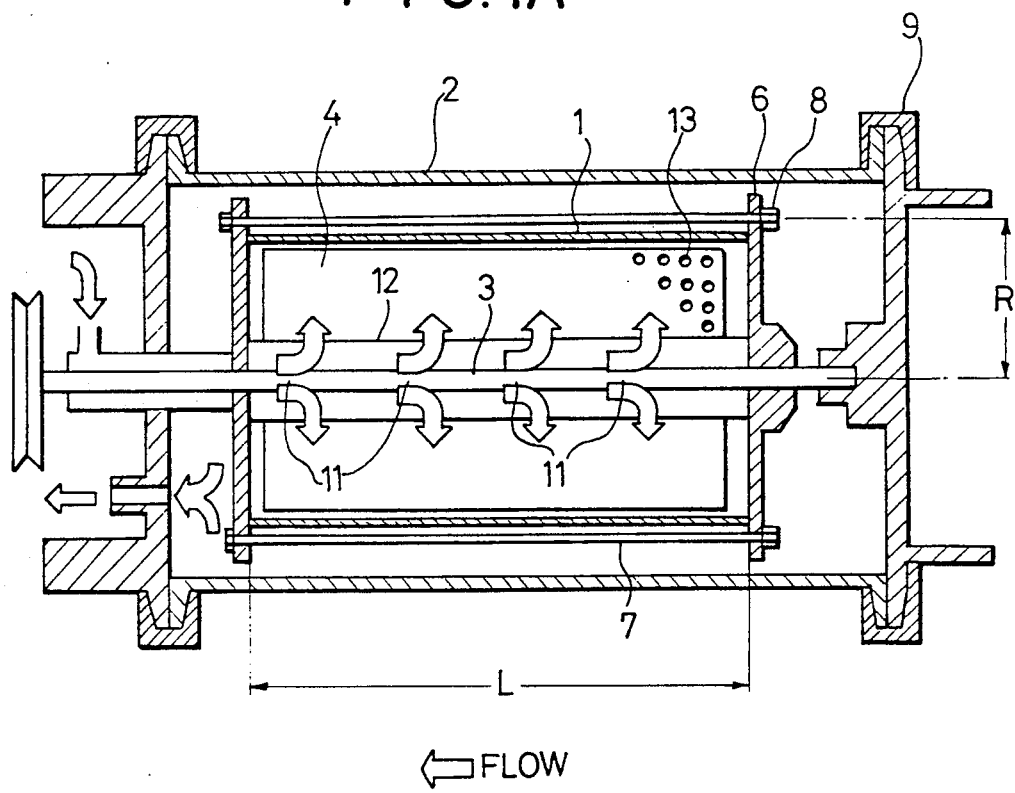
FIGS. 1A and 1B are schematic illustrations of an exemplary rotary column reactor suitable for carrying out the method of the present invention. In this FIG., 1A is a schematic sectional side elevation view of the reactor and 1B is a schematic sectional front elevation view of the rotary column. The reactor of FIGS. 1A and 1B consists of an inner cylinder (or carrier container section) 1, an outer cylinder 2, a hollow shaft 3, partition plates 4, a carrier 5, a gasket 6, through-bolts 7, nuts 8, clamps 9, a stream of fluid 10, orifices 11, a net 12 and openings 13.

The protein-containing fluids which can be used as feed fluids in the method of the present invention include, for example, skim milk, whole milk, whey, blood, microbial cultures, and animal or plant cell cultures; reconstituted fluids obtained by drying the foregoing fluids, as by spray drying, freeze-drying or the like, and then dissolving the residue in water or a suitable buffer solution; and biological crude extracts prepared from animal or plant tissues according to conventional procedure and containing a desired protein.

The term "protein" as used herein comprehends a wide variety of biologically active proteins, including the lactoferrin present in skim milk and whole milk, various enzymes (such as polynucleotide phosphorylate) present in blood platelets, lymphocytes and microbial cells, human $\beta$-interferon, and various antibodies, as well as protein complexes composed of two or more proteins.

The carriers which can be used in the method of the present invention to adsorb specifically such a protein present in the feed fluid include gel carriers (such as agarose, cellulose, silica, chitosan, acrylamide and other polymeric substances) having immobilized thereon a specific antigen or antibody, heparin, lectin, protein A or protein G; and the foregoing gel carriers having sulfate or other reactive groups on the molecule; and the like. The only requirement for the gel carrier is that an affinity for the desired protein or proteins. Thus, there may be used any of various well-known gel carriers that are being used as affinity gel carriers. Sulfonated polysaccharides, e.g., sulfonated cellulose and sulfonated chitosan, are preferred, especially for separating lactoferrin from milk and milk products.

The rotary column (hereinafter referred to briefly as the column) used in the present invention can be any rotating means for fluidizing the carrier contained in the column through the rotary motion of the column, and a fluid feeding mechanism which permits a feed fluid, comprising a protein-containing fluid, to be supplied to the column through orifices and brought into contact with the fluidized carrier.

By using a column having the above-described construction, the feed fluid is always brought into contact with the carrier while in a state of turbulent flow. Since this markedly promotes the reaction between them, it becomes possible to effect efficient adsorption of the protein on the carrier and carry out washing and elution procedures with a small volume of liquid. Generally, when it is desired to adsorb a desired protein on an affinity gel carrier, it is necessary to supply a small volume of feed fluid to the column at a low flow rate so as to increase the chance of contact between the feed fluid and the carrier surface. Otherwise, it would be difficult to effect satisfactory adsorption because the binding reaction of the protein with the reactive groups of the carrier surface due to its affinity for the protein does not proceed to a full extent. In contrast, the method of the present invention makes it possible to supply a larger volume of feed fluid to the column at a higher flow rate while securing satisfactory contact between the feed fluid and the carrier, owing to the fact that the carrier is fluidized by the rotary motion of the column and the feed fluid is introduced into the column through orifices. Moreover, since the carrier is not fluidized mechanically, no damage is caused to the carrier.

Figure 1B:
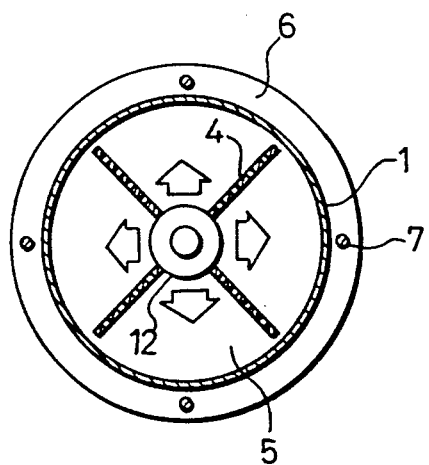

An examplary rotary column reactor which can be used in the present invention is illustrated in FIG. 1. Specifically, the column reactor includes a rotaty column comprising a carrier container section (or inner cylinder) 1 and an outer cylinder 2. Along a hollow shaft 3 having a plurality of orifices 11, the carrier container section 1 is divided by a plurality of partition plates 4 having openings 13 of appropriate size.

In addition, the conventional rotary column described in Japanese Patent Publication No. 43228/'81 can also be used in the method of the present invention.

The conditions required in the method of the present invention are more fully discussed hereinbelow.

The particle diameter of the carrier may be in the range of 10 $\mu$m to 7 mm and preferably in the range of 30 $\mu$m to 1 mm. If the particle diameter is smaller than 10 $\mu$m, the meshes of the carrier container section need to be reduced to a smaller size, which makes it difficult to disperse the feed fluid uniformly. On the other hand, if the particle diameter is larger than 7 mm, the effective surface area of the gel carrier becomes too small to be suitable for efficient recovery of proteins. Prior to use, the aforesaid gel carriers should preferably be pretreated so as to have a more or less uniform particle diameter distribution.

The hollow shaft 3 having orifices 11 communicating the carrier container section of the rotary column is preferably covered with a metal, cloth or nylon net 12 of appropriate mesh size. In this case, the mesh size is determined according to the particle diameter of the carrier. For example, when the carrier has a particle diameter of 150 $\mu$m, a net having a size of less than 100 mesh is used so that the carrier may not pass through the meshes of the net.

The carrier container section is divided by partition plates 4 having openings 13 of appropriate size, along the hollow shaft 3 having the orifices 11. When the volume of the carrier container section of the rotaty column is represented by $V_0$ (liters), the volume, $V_1$, of the carrier charged into the rotary column should be in the range of $V_0/200 \leq V_1 \leq V_0$ and preferably in the range of $0.1 V_0 \leq V_1 \leq 0.75 V_0$. If the volume, $V_1$, of the carrier is less than $1/200 V_0$, the volumes of the liquids used for washing and elution become large relative to the volume of the gel carrier, reducing the efficiency of recovery of the protein.

The column length t, L (cm), is preferably in the range of $L \geq (10^5 V_0)^{\frac{1}{3}}$. If L is shorter than $(10^5 V_0)^{\frac{1}{3}}$, the distribution of the fluid effluent from the orifices becomes non-uniform, making it difficult to agitate the feed fluid effectively.

In order to carry out efficiently the steps of causing the protein present in the feed fluid to become adsorbed on the carrier placed in the rotaty column having the above-described construction, washing the carrier, and recovering the protein by elution, the rotational speed, r, of the inner cylinder of the rotaty column should be in the range of 1 rpm $\leq$ r $\leq$ 1,000 rpm and preferably in the range of 5 rpm $\leq$ r $\leq$ 100 rpm. The actual rotational speed may be suitably determined according to the affinity of the carrier for the desired protein, the diameter of the carrier container section, and the like, so that the carrier can be fluidized without hindrance and brought into close contact with the protein-containing feed fluid being passed therethrough. If the rotational speed, r, of the inner cylinder of the rotary column is greater than 1,000 rpm, the fluidization of the carrier is hindered owing to the centrifugal force resulting from the rotation and, therefore, efficient contact between the feed fluid and the carrier is not effected.

The flow rate, $V_s$ (liters/hr), of the feed fluid being passed through the rotary column is preferably in the range of $V_s \leq 10^2 V_0$ (liters/hr). If $V_s$ is greater than $100 V_0$ (liters/hr), the efficiency of contact between the feed fluid (or protein-containing fluid) and the carrier is reduced and, therefore, the recovery of the protein from the feed fluid cannot be achieved efficiently. On the other hand, if the flow rate, $V_s$, is too low, the time required for the passage of the feed fluid is unduly prolonged, resulting in reduced efficiency. Moreover, the efficiency of contact between the feed fluid and the carrier is also reduced because the pressure change caused by the orifices is slight. Accordingly, the flow rate should be determined with due consideration for the rotational speed of the inner cylinder, the length of the column, the state of flow of the carrier, and the like.

Under the above-described conditions, the feed fluid can be brought into contact with the carrier in a state of turbulent flow.

It is to be understood that the passage of the feed fluid through the carrier may be carried out either in a circulating manner or in a single-pass manner.

Where the feed fluid is passed through the rotaty column in a circulating manner, the total passage time, T (hr), is governed by the concentration of the protein to be recovered, the flow rate, $V_s$ (liters/hr), of the fluid, and the adsorption capacity of the carrier. The passage time preferably satisfies the following condition:

$$T \leq 500 \frac{qV_1}{CV_s}$$

where C (g/liter) is the concentration in the feed fluid of the protein to be recovered, and q (g/liter of gel) is the saturated adsorption capacity of the carrier which is estimated by passing an excess of protein-containing fluid through the carrier.

If the aforesaid condition is not satisfied, i.e., $$T > 500 \frac{qV_1}{CV_s},$$

a reduction in efficiency will result because the feed fluid is passed through the rotary column in excess and the passage time is unduly prolonged. Usually, the passage of the feed fluid should be carried out within the above-defined time limit until the desired recovery is achieved.

In the method of the present invention, even a very small amount of protein present in a fluid can be efficiently adsorbed on a carrier by passing the fluid through the rotary column under the abovedescribed conditions and other properly-determined conditions such as temperature.

When the feed fluid is passed through the rotary column in the above-described manner, the desired protein present in the feed fluid is adsorbed on the carrier. Then, the carrier with the protein adsorbed thereon is washed within the rotary column in the same manner as described above for the adsorption procedure. For this purpose, a suitable washing liquid is used according to the characteristics of adsorption of the protein. For example, there may be used various washing liquids in conventional use in affinity chromatography, including water, suitable aqueous salt solutions (such as aqueous sodium chloride solutions) and suitable buffer solution (such as a 0.01M phosphate buffer solution containing 0.2M NaCl). The amount of washing liquid used at a time, $V_{wash}$ (liters), should preferably be in the range of $V_1 \leq V_{wash} < 100V_1$. The carrier may be washed one or more times either in a circulating manner or in a single-pass manner.

After washing, the desired protein adsorbed on the carrier can be eluted by passing through the rotary column a conventional eluent containing a substance which can break or weaken the bond between the desired protein and the reactive groups of the carrier. For this purpose, there may be used various eluents including, for example, suitable aqueous salt solutions (such as aqueous sodium chloride solutions) and suitable buffer solutions (such as phosphate buffer solutions useful for the above-described washing purpose). Generally, the eluent should be prepared according to the elution pattern of the desired protein, for example, so as to have a higher ionic strength than the washing liquid. If one or more proteins, in addition to the desired protein, are adsorbed on the carrier, the desired protein can be isolated according to any of well-known fractional elution techniques. The amount of eluent used, $V_{out}$ (liters), should be in the range of $V_1 \leq V_{out} < 100V_1$, and the eluent may be passed through the rotary column either in a circulating manner or in a single-pass manner.

It is to be noted in this connection that, by using the eluent in an amount of not greater than $100V_1$, more than about 95% of the desired protein adsorbed on the carrier can be eluted.

If necessary, the desired protein present in the eluate may be recovered in the form of a solid material or the like according to any conventional technique.

The present invention is further illustrated by the following examples.

EXAMPLE 1

A rotary column having an inner cylinder volume of 5 liters, an outer cylinder capacity of 20 liters and a column length of 265 cm was charged with 800 cc of sulfonated Cellulofine (Seikagahu Kogyo Co., Ltd., Tokyo, Japan) as a carrier gel. "Sulfonated Cellulofine" is a sulfonic ester gel of globular cellulose obtained by directly sulfonated spherical cellulose to introduce a sulfonic acid group at the 6-position carbon atom of some of the cellulose groups thereof. This carrier gel has a maximum lactoferrin adsorption of 3.0 mg/ml of gel.

While this rotary column was being rotated at a speed of 18 rpm, 100 liters of skim milk was passed therethrough once at a flow rate of 180 liters per hour.

Then, the above carrier gel having lactoferrin adsorbed thereon was washed four times with 20-liter portions of a 0.3M aqueous sodium chloride solution.

After washing, 20 liters of a 1M aqueous sodium chloride solution was circulated through the rotary column. Thus, the lactoferrin adsorbed on the carrier gel was recovered in a yield of 2.16 g.

The lactoferrin so recovered had a purity of 95%.

EXAMPLE 2

A rotary column similar to that used in Example 1 was charged with a carrier gel having monoclonal anti-lactoferrin antibody immobilized thereon. While this rotary column was being rotated at a speed of 18 rpm, 50 liters of the same skim milk as used in Example 1 was passed therethrough once at a flow rate of 180 liters per hour.

The antibody-immobilizing carrier gel used in this example has a maximum lactoferrin adsorption of 2.5 g/ml of gel.

Then, the carrier gel having lactoferrin adsorbed thereon was washed twice with 20-liter portions of a 0.5M aqueous sodium chloride solution, and three times with 20-liter portions of PBS.

After washing, 20 liters of a 0.2M acetate buffer solution (pH 3.7) was circulated through the column. Thus, the lactoferrin adsorbed on the carrier gel was recovered in a yield of 1.85 g (2.3 mg/ml of gel).

The lactoferrin so recovered had a purity of 98%.

EXAMPLE 3

A rotary column having an inner cylinder volume of 500 ml, an outer cylinder capacity of 600 ml and a column length of 130 cm was charged with 200 ml of sulfonated chitosan beads [having a maximum F-HA (a protein from Bordetella pertussis (strain Tohama, phase I) adsorption of 8 mg/ml of gel] as a carrier gel. This carrier gel was soaked in a 0.01M phosphate buffer solution containing 0.2M sodium chloride (pH 8.0; with a specific conductivity of about 17.5 ms/cm) and equilibrated therewith in the column. Thereafter, the buffer solution was discharged from the column.

On the other hand, 8 liters of the supernatant (with an F-HA content of 0.02%) of a culture obtained by cultivating the Bordetella Pertussis (strain Tohama, phase 1) in a fermenter was diluted so as to give a specific conductivity of about 17.5 ms/cm and a pH of 8.0. While the above rotary column was being rotated at a speed of 18 rpm, the diluted supernatant was circulated therethrough at a flow rate of 30 liters per hour for a period of 30 minutes.

Thereafter, the diluted supernatant was discharged from the column and the carrier gel was washed twice with 5-liter portions of the aforesaid buffer solution.

Then, 600 ml of a phosphate buffer solution (pH 7.6) containing 1.5M sodium chloride was passed through the column to elute the F-HA adsorbed on the carrier gel.

The recovery of the F-HA obtained by elution was 91.4%, and its degree of purification (i.e., the ratio of the specific activity of the purified F-HA fraction to the specific activity of the supernatant) was 32.

EXAMPLE 4

A rotary column having an inner cylinder volume of 500 ml, an outer cylinder capacity of 600 ml and a column length of 130 cm was charged with 200 ml of heparin-sepharose [having a maximum HBs antigen (derived from hepatitis B virus) adsorption of 8 mg/ml of gel] as a carrier gel. This carrier gel was equilibrated with a 0.027M McIlvaine buffer solution (pH 7.2) containing 0.05M sodium chloride.

On the other hand, 80 ml of human blood serum positive to a test for HBs antigen derived from hepatitis B virus was diluted with the aforesaid buffer solution to a volume of 600 ml. While the above rotary column was being rotated, the diluted serum was circulated therethrough at a flow rate of 30 liters per hour for a period of 30 minutes.

Thereafter, the carrier gel was thoroughly washed with 20-liter portions of the aforesaid buffer solution. Then, 600 ml of a 0.027M McIlvaine buffer solution (pH 7.2) containing 0.6M sodium chloride was passed through the column to elute the HBs antigen adsorbed on the carrier gel.

The recovery of the HBs antigen obtained by elution was 94.2%, based on its content in the serum.

The degree of purification of the recovered protein (i.e., the ratio of the amount of antigen to the total amount of protein) was as high as 14.3.

Although the invention has been described with preferred embodiments, it is to be understood that variations and modifications may be resorted to as will be apparent to those skilled in the art. Such variations and modifications are to be considered within the purview and the scope of the claims appended hereto.

We claim:

1. In a method for removing and recovering a specific protein or specific proteins from a protein-containing fluid by means of an affinity gel carrier having thereon a substance or group which imparts an affinity to the carrier for the protein, onto which the protein or proteins are absorbed, washed while absorbed thereon and eluted therefrom, the improvement which comprises the steps of charging a particulate affinity gel carrier having a particle size from 10 μm to 7 mm into a rotary column; passing the protein-containing fluid through the column by way of orifices while rotating the column to non-mechanically fluidize the carrier, whereby the fluid comes into contact with the carrier in a state of turbulent flow, until the protein contained therein becomes absorbed on the carrier; washing the column of fluidized carrier by passing a washing liquid through the fluidized carrier in the column being rotated; and eluting the desired protein from the washed column of fluid carrier by passing an eluent through the column being rotated without causing any significant damage to the carrier used to adsorb the protein thereon.

2. A method as claimed in claim 1 wherein the protein-containing fluid is lactoferrin-containing milk or lactoferrin-containing skim milk.

3. A method as claimed in claim 2 wherein the protein-containing fluid is lactoferrin-containing skim milk, the washing liquid is an aqueous sodium chloride solution, and the eluent is an aqueous sodium chloride solution.

4. The lactoferrin obtained by the method of claim 3 having a purity of about 80% or higher.

5. A method as claimed in claim 2 wherein the protein-containing fluid is lactoferrin-containing skim milk, the carrier is a carrier gel having monoclonal anti-lactoferrin antibody immobilized thereon, the washing liquid is an aqueous sodium chloride solution, and the eluent is an acetate buffer solution.

6. The lactoferrin obtained by the method of claim 5 and having a purity of about 90% or higher.

7. A method as claimed in claim 2 wherein the gel carrier is cellulose or chitosan having groups thereon which render the gel carrier effective for removing a specific protein or specific proteins from a protein-containing fluid.

8. A method as claimed in claim 7, wherein the groups are sulfate groups.

9. A method as claimed in claim 1 wherein the protein-containing fluid is passed through the column under the conditions:

$$L \geqq (10^5 V_0)^{\frac{1}{3}}$$

where $V_0$ (liters) is the volume of the carrier container section of the column.

(b) Rotational speed of column, r:

$$1\ \text{rpm} \leqq r \leqq 1{,}000\ \text{rpm}$$

(c) Flow rate, $V_s$ (liters/hr):

$$V_s \leqq 10^2 V_0\ \text{(liters/hr)}$$

(d) Passage time, T (hr):

$$T \leqq 500 \frac{qV_1}{CV_s}$$

where C (g/liter) is the concentration in the fluid of the protein to be recovered, q is the saturated adsorption capacity (g/liter of gel) of the carrier, and $V_1$ is the volume of carrier (liters) charged into the column.

10. A method as claimed in claim 9, wherein the protein-containing fluid is lactoferrin-containing milk or lactoferrin-containing skim milk; wherein the gel carrier is cellulose or chitosan having groups thereon which render the gel carrier effective for removing the lactoferrin from the milk; and wherein the washing liquid is an aqueous sodium chloride solution and the eluent is an aqueous sodium chloride solution.

* * * * *